United States Patent [19]

Hirota et al.

[11] Patent Number: 4,766,964

[45] Date of Patent: Aug. 30, 1988

[54] APPARENT DENSITY MEASURING DEVICE

[75] Inventors: Ryuichi Hirota, Miki; Shinichi Inoue, Kobe, both of Japan

[73] Assignee: Yamato Scale Company, Limited, Japan

[21] Appl. No.: 26,174

[22] Filed: Mar. 16, 1987

[30] Foreign Application Priority Data

May 2, 1986 [JP] Japan .................................. 61-102561

[51] Int. Cl.[4] ...................... G01G 13/00; G01G 19/52; G01N 9/02
[52] U.S. Cl. ........................................ 177/25; 177/50; 73/433
[58] Field of Search ..................... 177/25.14, 25.18, 50; 73/433–437

[56] References Cited

U.S. PATENT DOCUMENTS

| 923,560 | 6/1909 | Mount | 73/32 R |
| 2,373,026 | 4/1945 | Guyer et al. | 73/32 R X |
| 4,431,071 | 2/1984 | Magat e al. | 177/50 X |
| 4,548,286 | 10/1985 | Sashiki | 177/50 X |

Primary Examiner—George H. Miller, Jr.
Attorney, Agent, or Firm—Senniger, Powers, Leavitt and Roedel

[57] ABSTRACT

An apparant density measuring device for a weighing machine comprising a bucket having a known loading volume. Product is fed to the bucket in an amount sufficient to cause overflow from the bucket, the bucket being vibrated for a specific time during this feeding operation. After completion of the feeding operation, the loaded bucket is weighed.

9 Claims, 5 Drawing Sheets

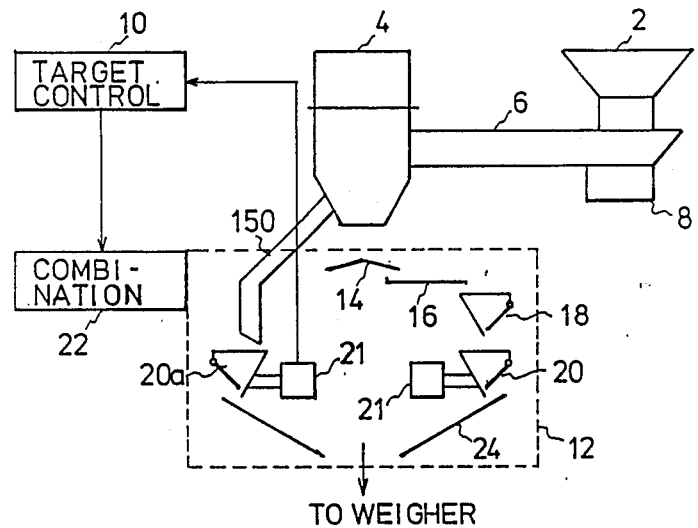
F I G. 11
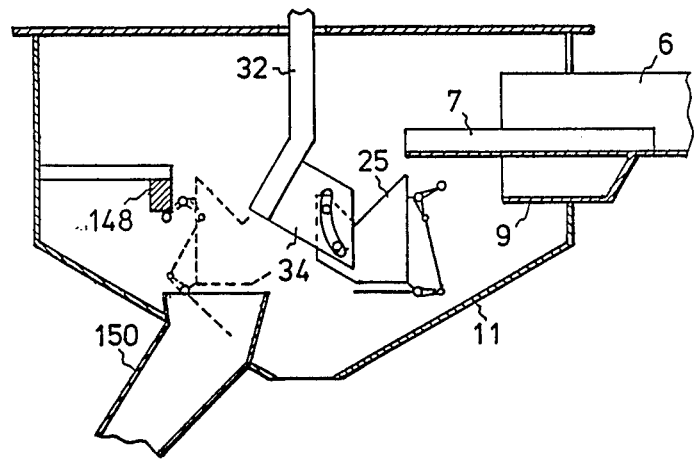
F I G. 12

APPARENT DENSITY MEASURING DEVICE

BACKGROUND OF INVENTION

This invention relates to an automatic apparent density measuring device which is especially effective for such product as potato chips or cornflakes having variable apparent density or specific gravity. The inventive device is useful when applied to an automatic weighing machine for weighing product in both weight and volume for the purpose of controlling a preset target weight based upon a measured density.

U.S. Pat. No. 4,548,286 discloses a combination weighing machine which can weigh out a quantity of product having a weight equal or approximate to a preset target weight and also a volume falling within a preset allowable range. This machine includes a plurality of weighing hoppers for weighing product and corresponding pool hoppers for temporarily holding a selected amount of product before feeding it to the weighing hoppers. One of the pool hoppers is provided with a photoelectric detector for detecting the level or height and consequently the volume of product fed therein. The detected volume is combined in a separate calculating unit with the corresponding weight measured by the underlying weighing hopper to obtain the apparent density. The calculated apparent density is supplied to a target weight control unit for controlling a preset target weight based upon the density so that the volume of each delivery of product from the machine falls within a preset allowable range.

However, the method and device for measuring apparent density in the above U.S. patent has the following disadvantages. First, measuring volume by detecting the height of product which has fallen naturally or spontaneously into the pool hopper from a feeding trough may be substantially imprecise especially when the product is variable in shape and particle size as in the case of fragile product such as cornflakes or potato chips. The error will be small when the product is uniform in shape and size; however, in this case the density should be uniform so that target weight control would not be needed. Second, there is a substantial chance of delivering a batch outside the allowable range of volume, for example, when a sudden change in density takes place, since the target weight control is effected on the basis of the density of current delivery.

SUMMARY OF THE INVENTION

Accordingly, an object of this invention is to improve accuracy of density measurement for product having variable apparent density by providing an improved density measuring device and method.

Another object of this invention is to provide an improved antomatic weighing system using such density measuring device for controlling target weight.

According to a feature of this invention, product to be weighed by a weighing device is sampled periodically before it is fed to the weighing device.

According to another feature of this invention, the sampling is effected by letting the product fall into a sampling bucket having a specific volume until excessive product overflows from the bucket to limit the volume of product therein with its inherent angle of slide.

According to a further feature of this invention, the sampling bucket is subjected to mechanical vibration for at least a part of the time of filling the sampling bucket.

Other features and operation of this invention will be described in more detail below with reference to the accompanying drawings.

BRIEF DESCRIPTION OF DRAWINGS

In the drawings:

FIG. 11 is a schematic side view representing a combination weighing machine having associated therewith a third embodiment of the density device;

FIG. 12 is a schematic sectional side view representing a mechanical structure of the device of FIG. 11.

Throughout the drawings, the same reference numerals are given to like or corresponding structural components.

DESCRIPTION OF PREFERRED EMBODIMENTS

Figure 1:
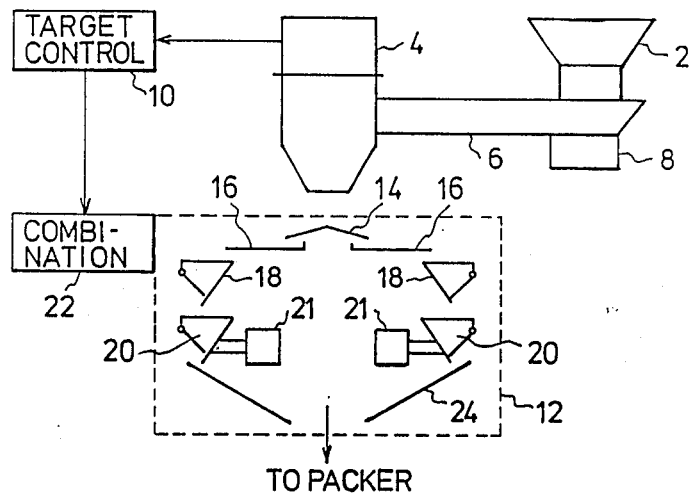
FIG. 1 is a schematic view representing a combination weighing machine having associated therewith a density measuring device according to this invention.

Referring to FIG. 1, an apparent density measuring device 4 is provided with a hopper 2 for holding a relatively large quantity of product to be weighed and a conventional vibration conveyer 6 driven by a suitable vibrator 8 for conveying the product from the hopper 2 to the device 4. The device 4 serves to sample a specific known volume of product from the conveyer 6 and weigh it to send the measured weight to a target weight control unit 10 which will be described later.

A conventional combination weighing machine 12 is disposed under the apparent density measuring device 4 for receiving the product discharged from the device 4. The combination weighing machine 12 includes a dispersion feeder 14 for receiving product from the device 4 and radially dispersing it for final distribution to a plurality of radial conveyer troughs 16. As is well known in the art, the dispersion feeder 14 and conveyer troughs 16 are vibrationally driven by known means, not shown, to feed a selected amount of product to each of underlying pool hoppers 18. Each pool hopper temporarily holds this amount of product and drops it into an underlying weigh hopper 20 in response to a command signal. The product in each weigh hopper 20 is weighed by an associated weigher 21 which provides the measured weight to a combination arithmetic unit 22. The unit 22 effects a so-called combination selecting operation with the measured weights from respective weighers 21, compares the resultant combination weights with a target weight fed from the target weight control unit 10; and discharges product from selected weigh hoppers 20 into a collection chute 24 for delivery to a succeeding step such as packing. No further description will be made on the combination weighing machine and process, since they are well known in the art and have no direct connection to this invention.

Figure 2:
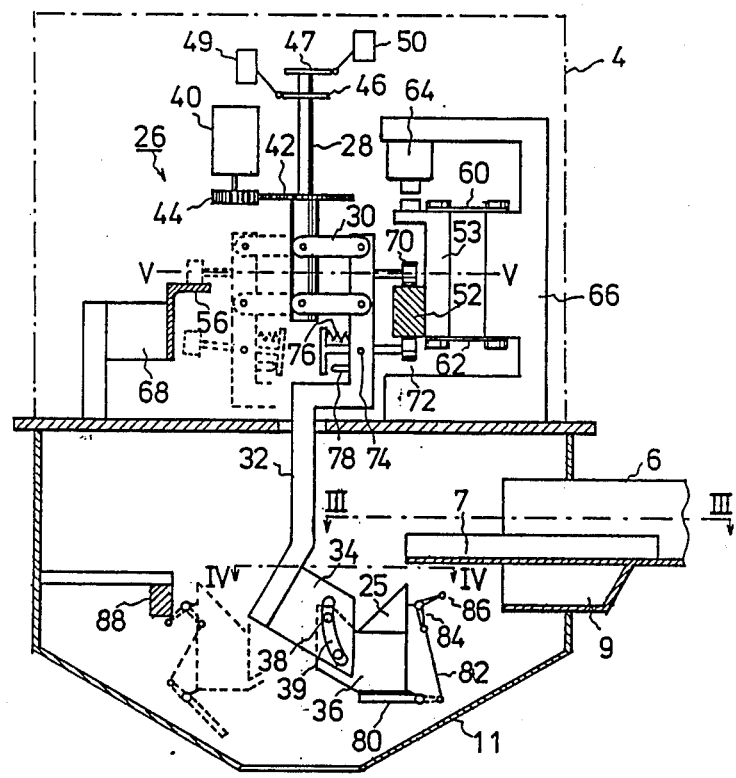
FIG. 2 is a schematic sectional side view representing a mechanical structure of the density measuring device embodied in FIG. 1.
Figure 3:
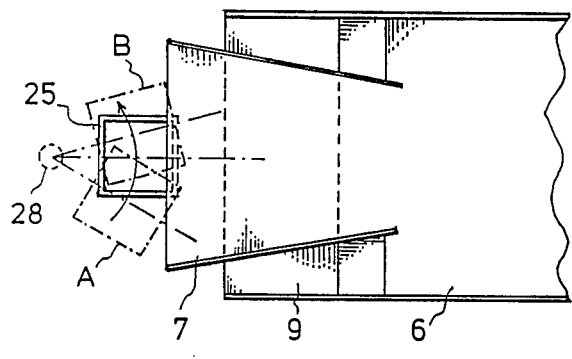
FIG. 3 is a partial plan view along line III—III of FIG. 2.

Now, the description will be made about a preferred embodiment of the apparent density measuring device 4 with reference to FIGS. 2 through 6. As shown in FIG. 2, the output end of the vibration conveyer 6 extends into the lower part of the device 4 and is divided into upper and lower floors 7 and 9. As shown in FIG. 3, the upper floor 7 widens in the forward (downstream) direction and the width at its root (i.e., upstream end) occupies only a part of the overall width of the conveyer 6, so that some of the product conveyed by the conveyer 6 progresses along the upper floor 7 and the remainder falls onto the lower floor 9. Product is conveyed along the upper and lower floors until it falls into a bottom chute 11 of the device 4 for delivery to the underlying combination weighing machine 12 (FIG. 1).

A sampling bucket 25 is disposed directly under the forward end of the upper floor 7 of the conveyor 6 and has a width less than the width of the forward end of the upper floor 7 for sampling a part of the product falling from that end, as shown in FIG. 3. As shown by an arrow in FIG. 3, the sampling bucket 25 revolves about the vertical axis of a rotating shaft 28 of a driving mechanism 26 and receives product during its passage under the forward end of upper floor 7. While the flow rate of product on the conveyer 6 will be limited by the demand of the associated combination weighing machine, it must be sufficient for causing overflow from the bucket 25. It will be understood in this regard that the volume of product sampled by the bucket 25 is determined by the angle of slide of the product, which is the maximum slope at which the product may be piled above the top of the bucket without sliding off the bucket. This "angle of slide" will vary from product to product. Therefore, the bucket dimension and revolving speed should be selected accordingly.

Figure 4:
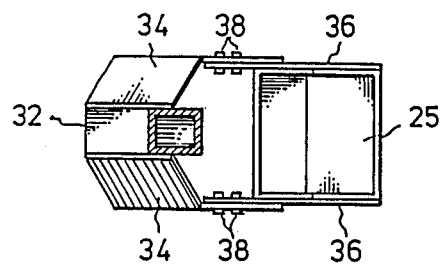
FIG. 4 is a partial sectional plan view along line IV—IV of FIG. 2.
Figure 5:
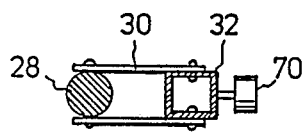
FIG. 5 is a partial sectional plan view along line V—V of FIG. 2.

As shown in FIG. 5, the rotating shaft 28 is coupled to a bucket hanger post 32 by a parallel-guiding linkage mechanism 30 and the bucket 25 is coupled to the post 32 by two pairs of coupling plates 34 and 36, as shown in FIG. 4. As shown, the coupling plates 34 fixed to the post 32 have curved slots 39 and the coupling plates 36 fixed to the bucket 25 have guide pins 38 received in the slots 39, for enabling optional adjustment of the inclination of bucket 25. As shown in FIG. 2, the side walls of the sampling bucket 25 are triangularly shaped and this shape and variable inclination of the bucket 25 make it possible to change the volumetric content of the bucket 25.

The rotation shaft 28 is continuously driven by a motor 40 through gears 42 and 44 and two cam plates 46 and 47 are fixed to this shaft 28 for actuating microswitches 49 and 50, respectively. The function of these cams and switches will be described later.

Figure 6:
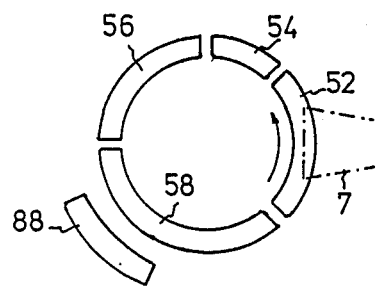
FIG. 6 is a plan view representing the guide rail configuration of the device of FIG. 2.

As shown in FIG. 6, four circular arc rails 52, 54, 56 and 58 are arranged coaxially with the rotating shaft 28. The rail 52 is disposed directly above the forward end of the upper conveyer floor 7 as shown in phantom in the drawing. As shown in FIG. 2, this rail 52 has a substantial thickness in the vertical direction and is fixed to a movable member 53 which is supported through leaf springs 60 and 62 by a bracket 66. The member 53 and, in turn, the rail 52 can be vibrated by means of an electromagnet 64 energized with a.c. power. The other rails 54, 56 and 58 are relatively thin. The rail 56 is supported by a load cell 68, while the rails 54 and 58 are directly fixed to the machine base.

A roller 70 is attached to the hanger post 32 so as to roll in a generally horizontal plane on these rails 52, 54, 56 and 58. Therefore, when the roller 70 is rolling on rail 56, the load cell 68 is loaded with the total weight of the hanger post 32, sampling bucket 25 and like for detecting the weight of product in the bucket 25. Another roller 72 is supported on a shaft which is pivoted at 74 on the hanger post 32, and is urged to the bottom face of the rail 52 by a spring 76 as shown in FIG. 2. Accordingly, while the roller 70 rolls on the rail 52, the hanger post 32 and the sampling bucket 25 are fixed vertically with respect to the vibrating member 53 to vibrate therewith. When the roller 52 is on the other rails, however, the lower roller 72 is maintained spaces from the rails by means of a stopper 78 as shown in phantom in FIG. 2.

The sampling bucket 25 has a gate door 80 for closing normally its bottom opening. The door 80 is linked through a connecting rod 82 to a lever 84 having a smaller roller 86 pivoted at its distal end. Another arcuate rail 88 is disposed coaxially with the aforementions rails 52 through 58, as shown in FIG. 6, so as to deflect the roller 86 to open the gate door 80 as shown in phantom, for discharging the contents of the bucket 25.

As described above, the sampling bucket 25 revolves under the upper floor 7 of the conveyer 6 as shown by the arrow in FIG. 3. The aforementioned cam plate 46 is shaped and arranged to actuate the associated microswitch 49 from position A to B (see FIG. 3) of the bucket 25 so that the electromagnet 64 is energized thereby to apply vertical vibration to the bucket 25 for this time interval. After the vibration ceases, additional product is fed to the bucket 25 until it overflows from the bucket. On the other hand, cam plate 47 is shaped and arranged to actuate the microswitch 50 when the roller 70 passes a point on rail 56 at which the weight signal of the load cell 68 becomes stable. The switch 50 serves to pass the weight signal to the target weight control unit 10.

As described above, the sampling bucket 25 of the inventive device is filled with product as uniformly as possible by the aid of vibration until product finally overflows from the bucket. It has been found that this process can substantially reduce the variance in measurements. The sampling operation may be effected periodically or on demand. The microswitch 50 may be interlocked with the conveyer 6 so as to prevent the weight signal from being delivered when no product is fed to the bucket 25.

Figure 7:
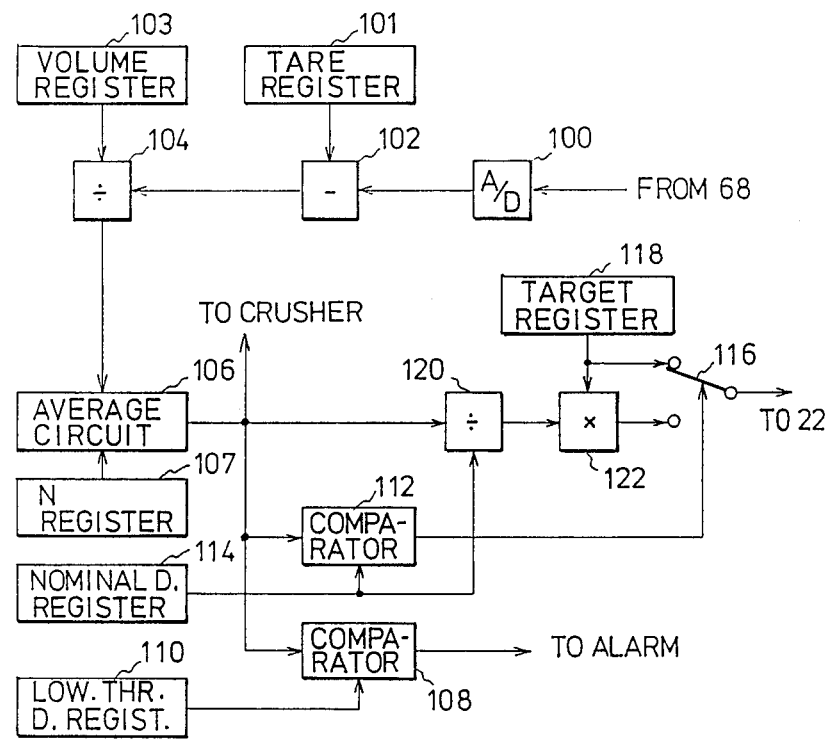
FIG. 7 is a schematic block diagram representing a circuit arrangement of a target weight control system to which the density measuring device is effectively applicable.

A preferred circuit arrangement of the target weight control unit 10 is shown in FIG. 7. The weight signal from the load cell 68 (FIG. 2) is digitized by an analog-to-digital (A/D) convertor 100 and applied to a subtracter 102. The subtracter 102 also receives from a tare register 101 a digital tare signal corresponding to the load applied to the load cell 68 when the sampling backet 25 is empty, and subtracts this signal from the weight signal from A/D convertor 100 to provide an output signal indicative of the weight of product in the bucket 25 to a divider 104.

A reference volume register 103 is previously loaded with a predetermined volume value which corresponds to an average volume of product necessary to fill the sampling bucket 25. The divider 104 divides the input weight signal by a reference volume signal from the register 103 to provide an apparent density signal. If a unit volume is adopted as the reference volume, the output of subtracter 102 can be used as the apparent density signal.

The apparent density signal is applied to an averaging circuit 106. This circuit 106 is arranged to always store N-number of input density signals by removing the oldest signal upon reception of a new signal, and to average the stored signals by N which is preset in a N-register 107, thereby providing an average density signal for target value control. The reason for using average density rather than the current density from the divider 104 for this purpose is to prevent excessive response of the control system. Therefore, this averaging process may be omitted according to circumstances.

The average density signal from the averaging circuit 106 is applied to a comparator 108 and compared with an allowable lower threshold density which is preset in a lower threshold density register 110. The lower threshold density is determined taking into consideration the volume of product which can be packed in a specified container without overflow and the least volume of product which must be packed in the container. The comparator 108 is arranged to provide a signal to a suitable alarm device (not shown) to actuate it when the average density is lower than the lower threshold density, thereby informing the operator of possible overflow of product from packages.

The average density signal from the averaging circuit 106 is also applied to another comparator 112 and compared with a nominal density which is preset in a nominal density register 114. The nominal density is determined based upon the normal weight and volume of product preferably packed in each package. The comparator 112 is arranged to provide a switching signal to a change-over switch 116 to turn its movable arm downward in the drawing when the average density is higher than the nominal density. Therefore, when the average density is not higher than the nominal density, a predetermined target weight set in a target weight register 118 is applied through the switch 116 to the combination arithmetic unit 22 (FIG. 1) for combination selection. Thus, the target weight for the unit 22 is left unchanged and the combination weighing machine continues its operation, so long as the current average density falls between the preset lower threshold and the nominal value.

The average density is further applied to another divider 120 which divides the average density by the nominal density from the register 114 to provide a correction coefficient to a multiplier 122. The multiplier 122 multiplies the target weight from the target weight register 118 by the correction coefficient to provide a corrected target weight. In other words, the target weight is raised with an increase in the average density when the average density is higher than the nominal density and indicates a shortage of the packing volume regardless of acceptable weight. In this case, the switch 116 is turned by the switching signal from the comparator 112, as described above, to apply the corrected raised target weight to the combination weighing machine, thereby raising the weight and, consequently, the volume of each package.

The average density signal may be supplied to a crusher (not shown) to control its crushing rate, thereby adjusting the apparent density of the product before it is fed to the combination weighing machine 12.

Figure 8:
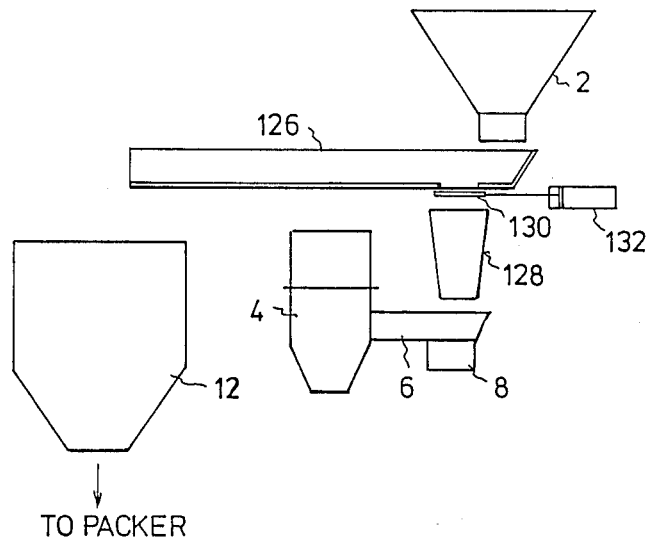
FIG. 8 is a schematic side view representing a weighing system including a second embodiment of the density measuring device.

FIG. 8 shows another embodiment in which product is fed from a hopper 2 through a vibration conveyer 126 to a combination weighing machine 12 and also sampled through a chute 128 by an apparent density measuring device 4 when a gate 130 in the bottom of the conveyer 126 is opened by an air cylinder 132. Therefore, the sampled product is not used in the machine 12 but discharged separately from the device 4.

Figure 9:
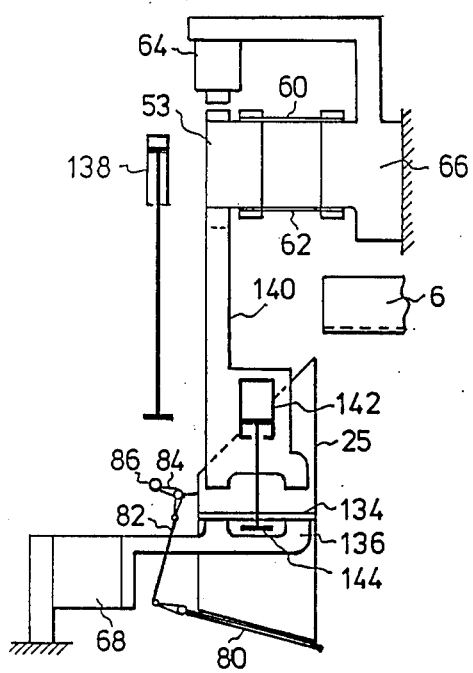
FIG. 9 is a schematic side view representing a mechanical structure of the device of FIG. 8.
Figure 10:
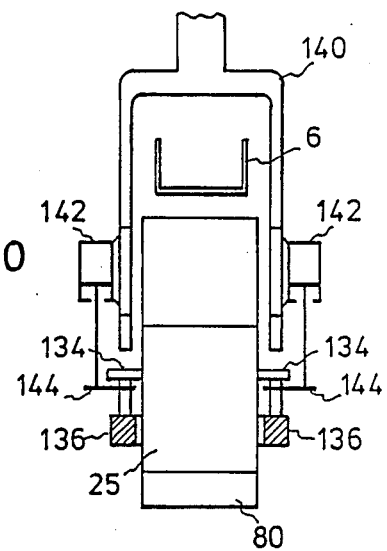
FIG. 10 is a partial front view of the device of FIGS. 8 and 9.

While the structure of this apparent density measuring device 4 may be similar to that as shown in FIG. 2, FIGS. 9 and 10 show a modified structure suitable for the device 4 of FIG. 8. This modification also includes a sampling bucket 25 fed from the conveyer trough 6 of FIG. 8. While the product feeding mode is similar to that of the structure of FIG. 2, the trough 6 need not be of double stage type. The bucket 25 has brackets 134 on both sides and is supported by these brackets 134 on a forked support 136 extending from a load cell 68 which is fixed to a machine frame. The bucket 25 also has a normally-closed bottom gate door 80 which can be opened by an air cylinder 138 through a linkage of connecting rod 82, lever 84 and roller 86.

Over the sampling bucket 25 is disposed a vibration mechanism including movable member 53, leaf springs 60 and 62, electromagnet 64 and bracket 66 as shown in FIG. 2. A forked member 140 extends downward from the movable member 53 so that its forked portions face corresponding portions of forked support 136. A pair of air cylinders 142 are attached to respective forked portions. pair of arms 114 fixed to the lower ends of piston rods of respective air cylinders 142 extend under the brackets 134 of the sampling bucket 25.

The device of FIGS. 9 and 10 operates as follows. The air cylinders 142 are actuated to raise the sampling bucket 25 to urge its brackets 134 against the bottom of the forked member 140 by the arms 144. Then, the gate 130 of FIG. 8 is opened and product is fed through the conveyer trough 6 into the sampling bucket 25 until it overflows therefrom. During a part of this feeding interval, the electromagnet 64 is energized to vibrate the bucket 25 as in the case of FIG. 2. After overflow of product from the bucket 25, the feed of product is interrupted and the bucket 25 is gently lowered onto the forked support 136, thereby causing the load cell 68 to produce a weight signal which is supplied for use in the circuit of FIG. 7 after it becomes stable through a suitable timing switch (not shown). Thereafter, the air cylinder 138 is actuated to open the gate 80 and discharge the weighed content, thereby restoring the initial condition.

Figure 13:
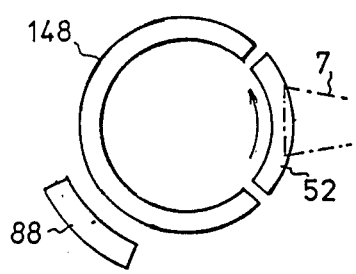
FIG. 13 is a plan view representing the guide rail configuration of the device of FIGS. 11 and 12.

A further modification of the device of FIG. 2 is shown in FIGS. 11, 12 and 13. In this modification, the sampled product (of a known volume) is weighed in a specific weigh hopper 20a of the combination weighing machine 12 by the associated weigher 21 and the weight signal therefrom is applied to the target weight control unit 10. Accordingly, the load cell 68 and weighing rail 56 are omitted and the rails 54 and 58 are united into a single stationary rail 148 as shown in FIGS. 12 and 13. An elongated chute 150 is provided for receiving the product discharged from the sampling bucket 25 and guiding it to weight hopper 20a. With this modification, it is possible not only to simplify the mechanical structure as described above, but also to simplify the control circuit by removing the tare compensating elements 101 and 102.

While the apparent density measuring device of this invention is applied to a combination weighing machine in the above description, this is not intended to be a limitation, and it shall be understood that the inventive device can be applied to any other weighing device of the same purpose.

We claim:

1. An apparent density measuring device for a weighing machine, comprising a bucket having a known loading volume, means for feeding product to be measured to said bucket in an amount sufficient to cause overflow therefrom, means for vibrating said bucket for a specific time during the feeding operation, and means for weighing the loaded bucket after completion of said feeding operation.

2. A device according to claim 1, characterized in that said feeding means is adapted to receive part of the product fed to said weighing machine and to feed it to said bucket.

3. An apparent density measuring device for a weighing machine, comprising a bucket having a known loading volume, means for feeding product to be measured to said bucket in an amount sufficient to cause overflow therefrom, means for vibrating said bucket for a specific time during the feeding operation, means for weighing the loaded bucket after completion of said feeding operation, and means for revolving said bucket in an orbit in a generally horizontal plane, said feeding, vibrating and weighing means being operable within respective predetermined segments of said orbit.

4. An apparent density measuring device for a weighing machine, comprising a bucket having a known loading volume, means for feeding product to be measured to said bucket in an amount sufficient to cause overflow therefrom, means for vibrating said bucket for a specific time during the feeding operation, means for weighing the loaded bucket after completion of said feeding operation, and means for vertically moving said bucket, said feeding and vibrating means being operable when said bucket is raised, and said weighing means being operable when said bucket is lowered.

5. A device according to claim 2, characterized in that said weighing machine is a combination weighing machine and said weighing means is one of the weighing units of said combination weighing machine.

6. An apparent density measuring device for a weighing machine, comprising a bucket having a known loading volume, means for feeding product to be measured to said bucket in an amount sufficient to cause overflow therefrom, means for vibrating said bucket for a specific time during the feeding operation, means for weighing the loaded bucket after completion of said feeding operation, and means for revolving said bucket in an orbit in a generally horizontal plane, said feeding, vibrating and weighing means being operable within respective predetermined segments of said orbit, said feeding and vibrating means being operable in segments different from said weighing means.

7. An apparent density measuring device for a weighing machine, comprising a bucket having a known loading volume, feeding means adapted to receive part of the product fed to said weighing machine and to feed it to said bucket, said feeding means being operable to feed the product to be measured to said bucket in an amount sufficient to cause overflow therefrom, means for vibrating said bucket for a specific time during the feeding operation, means for weighing the loaded bucket after completion of said feeding operation, and means for revolving said bucket in an orbit in a generally horizontal plane, said feeding, vibrating and weighing means being operable within respective predetermined segments of said orbit.

8. An apparent density measuring device for a weighing machine, comprising a bucket having a known loading volume, feeding means adapted to receive part of the product fed to said weighing machine and to feed it to said bucket, said feeding means being operable to feed the product to be measured to said bucket in an amount sufficient to cause overflow therefrom, means for vibrating said bucket for a specific time during the feeding operation, means for weighing the loaded bucket after completion of said feeding operation, and means for vertically moving said bucket, said feeding and vibrating means being operable when said bucket is raised, and said weighing means being operable when said bucket is lowered.

9. An apparent density measuring device for a weighing machine, comprising a bucket a known loading volume, feeding means adapted to receive part of the product fed to said weighing machine and to feed it to said bucket, said feeding means being operable to feed the product to be measured to said bucket in an amount sufficient to cause overflow therefrom, means for vibrating said bucket for a specific time during the feeding operation, means for weighing the loaded bucket after completion of said feeding operation, and means for revolving said bucket in an orbit in a generally horizontal plane, said feeding, vibrating and weighing means said orbit, said feeding and vibrating means being operable in segments different from said weighing means.

* * * * *

UNITED STATES PATENT AND TRADEMARK OFFICE
CERTIFICATE OF CORRECTION

PATENT NO.  : 4,766,964

DATED       : August 30, 1988

INVENTOR(S) : Ryuichi Hirota and Shinichi Inoue

It is certified that error appears in the above-identified patent and that said Letters Patent is hereby corrected as shown below:

Column 2, line 36, "the density device" should read --the density measuring device--.

Column 3, line 8, "unit 10; and discharges" should read --unit 10, and discharges--.

Column 3, line 43, "the angle of slide" should read --the "angle of slide"--.

Column 3, line 56, "slots 39, for enabling" should read --slots 39 for enabling--.

Column 8, claim 9, line 40, "a bucket a known" should read --a bucket having a known--.

Column 8, claim 9, lines 50-51, "means said orbit" should read --means being operable within respective predetermined segments of said orbit--.

Signed and Sealed this

Tenth Day of April, 1990

*Attest:*

HARRY F. MANBECK, JR.

*Attesting Officer*     *Commissioner of Patents and Trademarks*